United States Patent
Hughes et al.

(10) Patent No.: US 7,691,381 B2
(45) Date of Patent: Apr. 6, 2010

(54) STABILIZED BIODEGRADABLE NEUROTOXIN IMPLANTS

(75) Inventors: Patrick M. Hughes, Aliso Viejo, CA (US); Orest Olejnik, Coto De Caza, CA (US)

(73) Assignee: Allergan, Inc., Irvine, CA (US)

( * ) Notice: Subject to any disclaimer, the term of this patent is extended or adjusted under 35 U.S.C. 154(b) by 737 days.

(21) Appl. No.: 10/826,441

(22) Filed: Apr. 15, 2004

(65) Prior Publication Data
US 2005/0232966 A1 Oct. 20, 2005

(51) Int. Cl.
*A01N 37/18* (2006.01)
*A61K 39/02* (2006.01)
*A61K 39/08* (2006.01)
*A61K 39/38* (2006.01)

(52) U.S. Cl. ............... 424/184.1; 424/234.1; 424/236.1; 424/239.1; 514/2

(58) Field of Classification Search .............. 514/2
See application file for complete search history.

(56) References Cited

U.S. PATENT DOCUMENTS

| | | | | |
|---|---|---|---|---|
| 3,523,906 | A | 8/1970 | Masterman et al. | 424/427 |
| 3,691,090 | A | 9/1972 | Kitajima et al. | 252/316 |
| 3,737,337 | A | 6/1973 | Schnoring et al. | 427/212 |
| 4,389,330 | A | 6/1983 | Tice et al. | 427/213.36 |
| 4,853,224 | A | 8/1989 | Wong | 424/427 |
| 4,997,652 | A | 3/1991 | Wong | 424/428 |
| 5,019,400 | A | 5/1991 | Gomboty et al. | 424/497 |
| 5,164,188 | A | 11/1992 | Wong | 424/428 |
| 5,378,475 | A | 1/1995 | Smith et al. | 424/473 |
| 5,443,505 | A | 8/1995 | Wong et al. | 623/4 |
| 5,741,329 | A * | 4/1998 | Agrawal et al. | 424/423 |
| 5,989,545 | A | 11/1999 | Foster et al. | 424/183.1 |
| 6,217,895 | B1 | 4/2001 | Guo et al. | 424/427 |
| 6,281,015 | B1 | 8/2001 | Mooney et al. | 435/395 |
| 6,312,708 | B1 * | 11/2001 | Donovan | 424/423 |
| 6,440,460 | B1 * | 8/2002 | Gurny et al. | 424/486 |
| 6,506,399 | B2 | 1/2003 | Donovan | 424/423 |
| 6,548,078 | B2 | 4/2003 | Guo et al. | 424/423 |
| 2002/0009493 | A1 * | 1/2002 | Schwendeman et al. | 424/486 |
| 2002/0098237 | A1 | 7/2002 | Donovan et al. | 424/484 |
| 2003/0118598 | A1 | 6/2003 | Hunt | 424/184.1 |
| 2004/0033241 | A1 | 2/2004 | Donovan | 424/239.1 |

FOREIGN PATENT DOCUMENTS

WO  WO 01/58472 A  2/2001

OTHER PUBLICATIONS

Cheng, Cheng-Kuo et al., *Intravitreal Sustained-Release Dexamethasone Device in the Treatment of Experimental Uveitis*, Investigative Ophthalmology & Visual Science, Feb. 1995, vol. 36, No. 2, pp. 442-453.

Enyedi, Laura B. et al., *An intravitreal device providing sustained release of cyclosporine and dexamethasone*, Current Eye Research, Oct. 17, 1995, pp. 549-557.

Hainsworth, Dean P. et al., *Sustained Release Intravitreal Dexamethasone*, Journal of Ocular Pharmacology and Therapeutics, vol. 12, No. 1, 1996, pp. 57-63.

Kochinke, F. et al., *Biodegradable Drug Delivery System for Uveitis Treatment*, Investigative Ophthalmology & Visual Science, Feb. 15, 1996, vol. 37, No. 3, 186-B98.

Aoki, K., *Preclinical update on Botox® (botulinum toxin type A)-purified neurotoxin complex relative to other botulinum neurotoxin preparations*, Eur J Neurol Nov. 1999; 6(Suppl 4);S3-S10.

Bigalke H., et al., *Botulinum A Neurotoxin Inhibits Non-Cholinergic Synaptic Transmission in Mouse Spinal Cord Neurons in Culture*, Brain Research 360; 318-324:1985.

Bigalke H., et al., *Tetanus Toxin and Botulinum A Toxin Inhibit Release and Uptake of Various Transmitters, as Studied with Particulate Preparations From Rat Brain and Spinal Cord*, Naunyn-Schmiedeberg's Arch Pharmacol 316; 244-251:1981.

Coffield, J. et al., *The Site and Mechanism of Action of Botulinum Neurotoxin*, Therapy With Botulinum Toxin, Ed. Jankovic J. et al., Marcel Dekker, Inc., (1994), p. 5.

(Continued)

*Primary Examiner*—Mark Navarro
(74) *Attorney, Agent, or Firm*—Claude L. Nassif; Stephen Donovan

(57) ABSTRACT

Biodegradable neurotoxin implants and methods of making and using such implants are provided. Biodegradable neurotoxin implants include a neurotoxin, a biodegradable polymer component, and an acidity regulating component. The biodegradable polymer component is effective in controlling the release of the neurotoxin from the implant when the implant is located in a patient's body. The acidity regulating component is effective in maintaining a pH of the implant in a desired range that may be effective in stabilizing the neurotoxin as the implant biodegrades when the implant is located in a patient's body. In one embodiment, an implant includes a botulinum toxin, a biodegradable polymer, and either monomers from which a biodegradable polymer is derived or oligomers including monomeric units substantially identical to a monomer from which a biodegradable polymer is derived, or a combination of such monomers and oligomers. The oligomers and biodegradable polymer may be derived from a single type of monomer. The implants disclosed herein may be administered to a human or animal patient in which a therapeutic effect is desired for prolonged periods of time.

25 Claims, No Drawings

OTHER PUBLICATIONS

Gonelle-Gispert, C. et al., *SNAP-25a and -25b isoforms are both expressed in insulin-secreting cells and can function in insulin secretion*, Biochem J. (1999) 339:159-65.

Habermann E., et al., *Tetanus Toxin and Botulinum A and C Neurotoxins Inhibit Noradrenaline Release From Cultured Mouse Brain*, J Neurochem 51 (2);522-527:1988.

Habermann E., *Inhibition by Tetanus and Botulinum A Toxin of the Release of [$^3$H]Noradrenaline and [$^3$H]GABA From Rat Brain Homogenate*, Experientia 44 (1988); 224-226.

Habermann E., *I-Labeled Neurotoxin from Clostridium Botulinum A: Preparation, Binding to Synaptosomes and Ascent to the Spinal Cord*, Naunyn-Schmiedeberg's Arch. Pharmacol. (1974) 281; 47-56.

*Harrison's Principles of Internal Medicine*, edited by Anthony Fauci et al., 14.sup.th edition, published by McGraw Hill (1998).

Marchese Ragona, R. et al., *Management of Parotid Sialocele With Botulinum Toxin*, The Laryngoscope 109 (Aug. 1999);1344-1346.

*Movement Disorders* (1995), 10(3); 376.

Naumann, M. et al., *Botulinum toxin type A in the treatment of focal, axillary and palmar hyperhidrosis and other hyperhidrotic conditions*, European J. Neurology (1999) 6 (Supp 4): S111-S115.

Neimann et al., *Clostridial nurotixons: new tools for dissecting exocytosis*, Trends in Cell Biol. 4 (May 1994);179-185.

Pearce, L. B., *Pharmacologic Characterization of Botulinum Toxin For Basic Science and Medicine*, Toxicon (1997) 35(9); 1373-1412 at 1393.

Sanchez-Prieto, J., et al., *Botulinum Toxin A Blocks Glutamate Exocytosis From Guinea Pig Cerebral Cortical Synaptosomes*, Eur J. Biochem (1987) 165;675-681.

Schantz, E. J. et al, *Properties and Use of Botulinum Toxin and Other Microbial Neurotoxins in Medicine*, Microbiol Rev. (1992) 56; 80-99.

Singh, B., *Critical Aspects of Bacterial Protein Toxins*, pp. 63-84 (chapter 4) of Natural Toxins II, edited by B. R. Singh et al., Plenum Press, New York (1996).

Sloop, R. et al., *Reconstituted botulinum toxin type A does not lose potency in humans if it is refrozen or refrigerated for 2 weeks before use*, Neurology 48 (Jan. 1997);249-53.

Wiegand et al., *I-Labelled Botulinum A Neurotoxin: Pharmacokinetics in Cats after Intramuscular Injection*, Naunyn-Schmiedeberg's Arch. Pharmnacol. 292 (1976); 161-165.

\* cited by examiner

STABILIZED BIODEGRADABLE NEUROTOXIN IMPLANTS

The present invention relates to biodegradable implants. More particularly, the invention relates to biodegradable implants including a neurotoxin that is effective to provide a therapeutic effect to a human or animal patient.

Botulinum toxin type A is the most lethal natural biological agent known to man. Botulinum toxin type A is a polypeptide neurotoxin produced by the anaerobic, gram positive bacterium *Clostridium botulinum* and causes a neuroparalytic illness in humans and animals referred to as botulism. About 50 picograms of a commercially available botulinum toxin type A (available from Allergan, Inc., Irvine, Calif. under the tradename BOTOX® (purified neurotoxin complex) in 100 unit vials) is a $LD_{50}$ in mice (i.e. 1 unit). Thus, one unit of BOTOX contains about 50 picograms (about 56 attomoles) of botulinum toxin type A complex. Interestingly, on a molar basis, botulinum toxin type A is about 1.8 billion times more lethal than diphtheria, about 600 million times more lethal than sodium cyanide, about 30 million times more lethal than cobra toxin and about 12 million times more lethal than cholera. Singh, Critical Aspects of Bacterial Protein Toxins, pages 63-84 (chapter 4) of Natural Toxins II, edited by B. R. Singh et al., Plenum Press, New York (1996) (where the stated $LD_{50}$ of botulinum toxin type A of 0.3 ng equals 1 U is corrected for the fact that about 0.05 ng of BOTOX equals 1 unit). One unit (U) of botulinum toxin is defined as the $LD_{50}$ upon intraperitoneal injection into female Swiss Webster mice weighing 18 to 20 grams each.

Neurotransmitters are packaged in synaptic vesicles within the cytoplasm of neurons and are then transported to the inner plasma membrane where the vesicles dock and fuse with the plasma membrane. Studies of nerve cells employing clostridial neurotoxins as probes of membrane fusion have revealed that fusion of synaptic vesicles with the cell membrane in nerve cells depends upon the presence of specific proteins that are associated with either the vesicle or the target membrane. These proteins have been termed SNAREs. A protein alternatively termed synaptobrevin or VAMP (vesicle-associated membrane protein) is a vesicle-associated SNARE (v-SNARE). There are at least two isoforms of synaptobrevin; these two isoforms are differentially expressed in the mammalian central nervous system, and are selectively associated with synaptic vesicles in neurons and secretory organelles in neuroendocrine cells. The target membrane-associated SNAREs (t-SNARES) include syntaxin and SNAP-25. Following docking, the VAMP protein forms a core complex with syntaxin and SNAP-25; the formation of the core complex appears to be an essential step to membrane fusion. See Neimann et al., Trends in Cell Biol. 4:179-185: 1994.

Seven generally immunologically distinct botulinum neurotoxins have been characterized, these being respectively botulinum neurotoxin serotypes A, B, $C_1$, D, E, F and G each of which is distinguished by neutralization with type-specific antibodies. The different serotypes of botulinum toxin vary in the animal species that they affect and in the severity and duration of the paralysis they evoke. For example, it has been determined that botulinum toxin type A is 500 times more potent, as measured by the rate of paralysis produced in the rat, than is botulinum toxin type B. Additionally, botulinum toxin type B has been determined to be non-toxic in primates at a dose of 480 U/kg which is about 12 times the primate $LD_{50}$ for botulinum toxin type A. Botulinum toxin apparently binds with high affinity to cholinergic motor neurons, is translocated into the neuron and blocks the release of acetylcholine.

Regardless of serotype, the molecular mechanism of toxin intoxication appears to be similar and to involve at least three steps or stages. In the first step of the process, the toxin binds to the presynaptic membrane of the target neuron through a specific interaction between the heavy chain, H chain, and a cell surface receptor; the receptor is thought to be different for each type of botulinum toxin and for tetanus toxin. The carboxyl end segment of the H chain, $H_C$, appears to be important for targeting of the toxin to the cell surface.

In the second step, the toxin crosses the plasma membrane of the poisoned cell. The toxin is first engulfed by the cell through receptor-mediated endocytosis, and an endosome containing the toxin is formed. The toxin then escapes the endosome into the cytoplasm of the cell. This step is thought to be mediated by the amino end segment of the H chain, $H_N$, which triggers a conformational change of the toxin in response to a pH of about 5.5 or lower. Endosomes are known to possess a proton pump which decreases intra-endosomal pH. The conformational shift exposes hydrophobic residues in the toxin, which permits the toxin to embed itself in the endosomal membrane. The toxin (or at a minimum the light chain) then translocates through the endosomal membrane into the cytoplasm.

The last step of the mechanism of botulinum toxin activity appears to involve reduction of the disulfide bond joining the heavy chain, H chain, and the light chain, L chain. The entire toxic activity of botulinum and tetanus toxins is contained in the L chain of the holotoxin; the L chain is a zinc ($Zn^{++}$) endopeptidase which selectively cleaves proteins essential for recognition and docking of neurotransmitter-containing vesicles with the cytoplasmic surface of the plasma membrane, and fusion of the vesicles with the plasma membrane. Tetanus neurotoxin, and botulinum toxins B, D, F and G cause degradation of synaptobrevin (also called vesicle-associated membrane protein (VAMP)), a synaptosomal membrane protein. Most of the VAMP present at the cytoplasmic surface of the synaptic vesicle is removed as a result of any one of these cleavage events. Serotype A and E cleave SNAP-25. Serotype C, was originally thought to cleave syntaxin, but was found to cleave syntaxin and SNAP-25. Each toxin specifically cleaves a different bond (except tetanus and type B which cleave the same bond).

Botulinum toxins have been used in clinical settings for the treatment of neuromuscular disorders characterized by hyperactive skeletal muscles. Botulinum toxin type A was approved by the U.S. Food and Drug Administration in 1989 for the treatment of blepharospasm, strabismus and hemifacial spasm. Non-type A botulinum toxin serotypes apparently have a lower potency and/or a shorter duration of activity as compared to botulinum toxin type A. Clinical effects of peripheral intramuscular botulinum toxin type A are usually seen within one week of injection. The typical duration of symptomatic relief from a single intramuscular injection of botulinum toxin type A averages about three months.

Although all the botulinum toxin serotypes apparently inhibit release of the neurotransmitter acetylcholine at the neuromuscular junction, they do so by affecting different neurosecretory proteins and/or cleaving these proteins at different sites. For example, botulinum types A and E both cleave the 25 kiloDalton (kD) synaptosomal associated protein (SNAP-25), but they target different amino acid sequences within this protein. Botulinum toxin types B, D, F and G act on vesicle-associated protein (VAMP, also called synaptobrevin), with each serotype cleaving the protein at a different site. Finally, botulinum toxin type $C_1$ has been shown to cleave both syntaxin and SNAP-25. These differences in mechanism of action may affect the relative potency and/or duration of action of the various botulinum toxin serotypes. Apparently, a substrate for a botulinum toxin can be found in a variety of different cell types. See e.g. Biochem, J 1;339 (pt 1):159-65:1999, and Mov Disord, 10(3): 376:1995 (pancreatic islet B cells contain at least SNAP-25 and synaptobrevin).

The molecular weight of the botulinum toxin protein molecule, for all seven of the known botulinum toxin serotypes, is about 150 kD. Interestingly, the botulinum toxins are released by Clostridial bacterium as complexes comprising the 150 kD botulinum toxin protein molecule along with associated non-toxin proteins. Thus, the botulinum toxin type A complex can be produced by Clostridial bacterium as 900 kD, 500 kD and 300 kD forms. Botulinum toxin types B and $C_1$ is apparently produced as only a 700 kD or 500 kD complex. Botulinum toxin type D is produced as both 300 kD and 500 kD complexes. Finally, botulinum toxin types E and F are produced as only approximately 300 kD complexes. The complexes (i.e. molecular weight greater than about 150 kD) are believed to contain a non-toxin hemaglutinin protein and a non-toxin and non-toxic nonhemaglutinin protein. These two non-toxin proteins (which along with the botulinum toxin molecule comprise the relevant neurotoxin complex) may act to provide stability against denaturation to the botulinum toxin molecule and protection against digestive acids when toxin is ingested. Additionally, it is possible that the larger (greater than about 150 kD molecular weight) botulinum toxin complexes may result in a slower rate of diffusion of the botulinum toxin away from a site of intramuscular injection of a botulinum toxin complex.

In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine (Habermann E., et al., Tetanus Toxin and Botulinum A and C Neurotoxins Inhibit Noradrenaline Release From Cultured Mouse Brain, J Neurochem 51 (2);522-527:1988) CGRP, substance P and glutamate (Sanchez-Prieto, J., et al., Botulinum Toxin A Blocks Glutamate Exocytosis From Guinea Pig Cerebral Cortical Synaptosomes, Eur J. Biochem 165;675-681 :1987). Thus, when adequate concentrations are used, stimulus-evoked release of most neurotransmitters is blocked by botulinum toxin. See e.g. Pearce, L. B., Pharmacologic Characterization of Botulinum Toxin For Basic Science and Medicine, Toxicon 35(9); 1373-1412 at 1393 (1997); Bigalke H., et al., Botulinum A Neurotoxin Inhibits Non-Cholinergic Synaptic Transmission in Mouse Spinal Cord Neurons in Culture, Brain Research 360;318-324:1985; Habermann E., Inhibition by Tetanus and Botulinum A Toxin of the Release of [$^3$H]Noradrenaline and [$^3$H]GABA From Rat Brain Homogenate, Experientia 44;224-226: 1988, Bigalke H., et al., Tetanus Toxin and Botulinum A Toxin Inhibit Release and Uptake of Various Transmitters, as Studied with Particulate Preparations From Rat Brain and Spinal Cord, Naunyn-Schmiedeberg's Arch Pharmacol 316;244-251:1981, and; Jankovic J. et al., Therapy With Botulinum Toxin, Marcel Dekker, Inc., (1994), page 5.

Botulinum toxin type A can be obtained by establishing and growing cultures of Clostridium botulinum in a fermenter and then harvesting and purifying the fermented mixture in accordance with known procedures. All the botulinum toxin serotypes are initially synthesized as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes $C_1$, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture. Therefore, a certain percentage of any preparation of, for example, the botulinum toxin type B toxin is likely to be inactive, possibly accounting for the known significantly lower potency of botulinum toxin type B as compared to botulinum toxin type A. The presence of inactive botulinum toxin molecules in a clinical preparation will contribute to the overall protein load of the preparation, which has been linked to increased antigenicity, without contributing to its clinical efficacy. Additionally, it is known that botulinum toxin type B has, upon intramuscular injection, a shorter duration of activity and is also less potent than botulinum toxin type A at the same dose level.

High quality crystalline botulinum toxin type A can be produced from the Hall A strain of Clostridium botulinum with characteristics of $\geq 3. \times 10^7$ U/mg, an $A_{260}/A_{278}$ of less than 0.60 and a distinct pattern of banding on gel electrophoresis. The known Shantz process can be used to obtain crystalline botulinum toxin type A, as set forth in Shantz, E. J., et al, Properties and Use of Botulinum Toxin and Other Microbial Neurotoxins in Medicine, Microbiol Rev. 56;80-99:1992. Generally, the botulinum toxin type A complex can be isolated and purified from an anaerobic fermentation by cultivating Clostridium botulinum type A in a suitable medium. The known process can also be used, upon separation out of the non-toxin proteins, to obtain pure botulinum toxins, such as for example: purified botulinum toxin type A with an approximately 150 kD molecular weight with a specific potency of $1-2 \times 10^8$ $LD_{50}$ U/mg or greater; purified botulinum toxin type B with an approximately 156 kD molecular weight with a specific potency of $1-2 \times 10^8$ $LD_{50}$ U/mg or greater, and; purified botulinum toxin type F with an approximately 155 kD molecular weight with a specific potency of $1-2 \times 10^7$ $LD_{50}$ U/mg or greater.

Botulinum toxins and/or botulinum toxin complexes can be obtained from various sources, including List Biological Laboratories, Inc., Campbell, Calif.; the Centre for Applied Microbiology and Research, Porton Down, U.K.; Wako (Osaka, Japan), Metabiologics (Madison, Wis.) as well as from Sigma Chemicals of St. Louis, Mo.

Pure botulinum toxin is so labile that it is generally not used to prepare a pharmaceutical composition. Furthermore, the botulinum toxin complexes, such as the toxin type A complex are also extremely susceptible to denaturation due to surface denaturation, heat and alkaline conditions. Inactivated toxin forms toxoid proteins which can be immunogenic. The resulting antibodies can render a patient refractory to toxin injection.

As with enzymes generally, the biological activities of the botulinum toxins (which are intracellular peptidases) are dependent, at least in part, upon their three dimensional conformation. Thus, botulinum toxin type A is detoxified by heat, various chemicals surface stretching and surface drying. Additionally, it is known that dilution of the toxin complex obtained by the known culturing, fermentation and purification to the much, much lower toxin concentrations used for pharmaceutical composition formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Additionally, the toxin may be used months or years after the toxin containing pharmaceutical composition is formulated. Significantly, it is known that the toxin can be stabilized during the manufacture and compounding processes as well as during storage by use of a stabilizing agent such as albumin and gelatin.

The commercially available botulinum toxin sold under the trademark BOTOX (available from Allergan, Inc., of Irvine, Calif.) consists of a freeze-dried, purified botulinum toxin type A complex, albumin and sodium chloride packaged in sterile, vacuum-dried form. The botulinum toxin type A is made from a culture of the Hall strain of *Clostridium botulinum* grown in a medium containing N-Z amine and yeast extract. The botulinum toxin type A complex is purified from the culture solution by a series of acid precipitations to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. The vacuum-dried product is stored in a freezer at or below −5° C. BOTOX can be reconstituted with sterile, non-preserved saline prior to intramuscular injection. Each vial of BOTOX contains about 100 units (U) of *Clostridium botulinum* toxin type A purified neurotoxin complex, 0.5 milligrams of human serum albumin and 0.9 milligrams of sodium chloride in a sterile, vacuum-dried form without a preservative.

To reconstitute vacuum-dried BOTOX, sterile normal saline without a preservative (0.9% Sodium Chloride Injection) is used by drawing up the proper amount of diluent in the appropriate size syringe. Since BOTOX may be denatured by bubbling or similar violent agitation, the diluent is gently injected into the vial. For sterility reasons BOTOX is preferably administered within four hours after the vial is removed from the freezer and reconstituted. During these four hours, reconstituted BOTOX can be stored in a refrigerator at about 2° C. to about 8° C. Reconstituted, refrigerated BOTOX retains its potency for at least two weeks. Neurology, 48:249-53:1997.

It has been reported that botulinum toxin type A has been used in various clinical settings, including the following:

(1) about 75-125 units of BOTOX per intramuscular injection (multiple muscles) to treat cervical dystonia;

(2) 5-10 units of BOTOX per intramuscular injection to treat glabellar lines (brow furrows) (5 units injected intramuscularly into the procerus muscle and 10 units injected intramuscularly into each corrugator supercihii muscle);

(3) about 30-80 units of BOTOX to treat constipation by intrasphincter injection of the puborectalis muscle;

(4) about 1-5 units per muscle of intramuscularly injected BOTOX to treat blepharospasm by injecting the lateral pretarsal orbicularis oculi muscle of the upper lid and the lateral pre-tarsal orbicularis oculi of the lower lid.

(5) to treat strabismus, extraocular muscles have been injected intramuscularly with between about 1-5 units of BOTOX, the amount injected varying based upon both the size of the muscle to be injected and the extent of muscle paralysis desired (i.e. amount of diopter correction desired).

(6) to treat upper limb spasticity following stroke by intramuscular injections of BOTOX into five different upper limb flexor muscles, as follows:
(a) flexor digitorum profundus: 7.5 U to 30 U
(b) flexor digitorum sublimus: 7.5 U to 30 U
(c) flexor carpi ulnaris: 10 U to 40 U
(d) flexor carpi radialis: 15 U to 60 U
(e) biceps brachii: 50 U to 200 U.
Each of the five indicated muscles has been injected at the same treatment session, so that the patient receives from 90 U to 360 U of upper limb flexor muscle BOTOX by intramuscular injection at each treatment session.

(7) to treat migraine, pericranial injected (injected symmetrically into glabellar, frontalis and temporalis muscles) injection of 25 U of BOTOX has showed significant benefit as a prophylactic treatment of migraine compared to vehicle as measured by decreased measures of migraine frequency, maximal severity, associated vomiting and acute medication use over the three month period following the 25 U injection.

It is known that botulinum toxin type A can have an efficacy for up to 12 months (European J. Neurology 6 (Supp 4): S111-S1150:1999), and in some circumstances for as long as 27 months, (The Laryngoscope 109: 1344-1346:1999). However, the usual duration of the paralytic effect of an intramuscular injection of BOTOX is typically about 3 to 4 months.

The success of botulinum toxin type A to treat a variety of clinical conditions has led to interest in other botulinum toxin serotypes. A study of two commercially available botulinum type A preparations (BOTOX and DYSPORT®) and preparations of botulinum toxins type B and F (both obtained from Wako Chemicals, Japan) has been carried out to determine local muscle weakening efficacy, safety and antigenic potential. Botulinum toxin preparations were injected into the head of the right gastrocnemius muscle (0.5 to 200.0 units/kg) and muscle weakness was assessed using the mouse digit abduction scoring assay (DAS). $ED_{50}$ values were calculated from dose response curves. Additional mice were given intramuscular injections to determine $LD_{50}$ doses. The therapeutic index was calculated as $LD_{50}/ED_{50}$. Separate groups of mice received hind limb injections of BOTOX (5.0 to 10.0 units/kg) or botulinum toxin type B (50.0 to 400.0 units/kg), and were tested for muscle weakness and increased water consumption, the later being a putative model for dry mouth. Antigenic potential was assessed by monthly intramuscular injections in rabbits (1.5 or 6.5 ng/kg for botulinum toxin type B or 0.15 ng/kg for BOTOX). Peak muscle weakness and duration were dose related for all serotypes. DAS $ED_{50}$ values (units/kg) were as follows: BOTOX: 6.7, DYSPORT: 24.7, botulinum toxin type B: 27.0 to 244.0, botulinum toxin type F: 4.3. BOTOX had a longer duration of action than botulinum toxin type B or botulinum toxin type F. Therapeutic index values were as follows: BOTOX: 10.5, DYSPORT: 6.3, botulinum toxin type B: 3.2. Water consumption was greater in mice injected with botulinum toxin type B than with BOTOX, although botulinum toxin type B was less effective at weakening muscles. After four months of injections 2 of 4 (where treated with 1.5 ng/kg) and 4 of 4 (where treated with 6.5 ng/kg) rabbits developed antibodies against botulinum toxin type B. In a separate study, 0 of 9 BOTOX treated rabbits demonstrated antibodies against botulinum toxin type A. DAS results indicate relative peak potencies of botulinum toxin type A being equal to botulinum toxin type F, and botulinum toxin type F being greater than botulinum toxin type B. With regard to duration of effect, botulinum toxin type A was greater than botulinum toxin type B, and botulinum toxin type B duration of effect was greater than botulinum toxin type F. As shown by the therapeutic index values, the two commercial preparations of botulinum toxin type A (BOTOX and DYSPORT) are different. The increased water consumption behavior observed following hind limb injection of botulinum toxin type B indicates that clinically significant amounts of this serotype entered the murine systemic circulation. The results also indicate that in order to achieve efficacy comparable to botulinum toxin type A, it is necessary to increase doses of the other serotypes examined. Increased dosage can comprise safety. Furthermore, in rabbits, type B was more antigenic than was BOTOX, possibly because of the higher protein load injected to achieve an effective dose of botulinum toxin type B. Eur J Neurol 1999 November; 6(Suppl 4):S3-S10.

In addition to having pharmacologic actions at a peripheral location, a botulinum toxin can also exhibit a denervation effect in the central nervous system. Wiegand et al, Naunyn-Schmiedeberg's Arch. Pharmacol. 1976;292, 161-165, and Habermann, Naunyn-Schmiedeberg's Arch. Pharmacol. 1974;281, 47-56 reported that botulinum toxin is able to ascend to the spinal area by retrograde transport. As such, a botulinum toxin injected at a peripheral location, for example intramuscularly, can potentially be retrograde transported to the spinal cord.

U.S. Pat. No. 5,989,545 discloses that a modified clostridial neurotoxin or fragment thereof, preferably a botulinum toxin, chemically conjugated, or recombinantly fused to a particular targeting moiety can be used to treat pain by administration of the agent to the spinal cord.

Typically, therapeutic use of a botulinum toxin is by subcutaneous or intramuscular injection of an aqueous solution of a botulinum toxin type A or B. A repeat injection can b administered every 2-4 months to maintain a terapeutic efficacy of the toxin (i.e. a reduction of muscle spasm at or in the vicinity of the injection site). Each administration of a dose of a botulinum toxin to a patient therefore requires the patient to present himself to his physician at regular intervals. Unfortunately, patients can forget or be unable to attend appointments and physician schedules can make regular, periodic care over a multiyear period difficult to consistently maintain. Additionally, the requirement for 3-6 toxin injections per year on an ongoing basis increases the risk of infection or of misdosing the patient.

Sustained, pulsatile or multiphasic delivery of pharmaceutically active compounds from bioerodible drug delivery systems is known. Release kinetics of therapeutic agents in such drug delivery systems can be controlled by diffusion of the therapeutically active agent within a polymer matrix and subsequent counter diffusion of water, via chemical degradation of the delivery system, or chemical or solvent activation. An external stimulus can also control release of such therapeutic agents. Examples of such stimuli include electric current, ultrasound, light, or thermal factors.

Bioerodible polymers can be used to form monolithic homogeneous or heterogeneous implants and microparticulates, membrane controlled implants or microparticulates, multistage delivery systems or a combinations of these. Polymers of such implants can be natural or synthetic and may include polyesters, poly (ortho esters) or polyanhydrides. Specific polymers include poly-lactic acid (PLA), poly (lactide-co-glycolide) (PLGA), Poly-L-lactic acid (PLLA), polycaprolactone and poly (ortho acetate).

PLGA and PLA implants degrade by hydrolysis of their ester bonds. These polyesters degrade by bulk erosion and require an initial diffusion of water into the polymer prior to hydrolysis. Polymer variables that affect degradation includes poly (lactide-co-glycolide) monomer ratios, degree of crystallinity, enantiomeric composition of the polymer, degree of implant hydrophobicity, polymer molecular weight, the percent free carboxylic acid end groups and the presence of catalysts. The mechanism of hydrolysis involves hydration, followed by random chain scission without loss of molecular weight and finally degradation into the lactic acid and glycolic acid monomers once the molecular weight of the polymer approaches twenty percent of its original value. The free carboxylic end caps of the degrading polymer may slightly lower the pH of the polymer microenvironment. However, the rate of increase in microenvironment acidity is variable due to the non-homogenous and random nature of initial chain scission. Complete degradation drives the pH of the polymer system down to 3 to 4.

Acid and basic excipients have been incorporated into PLGA, poly (ortho ester) and other polyester polymers to catalyze polymer degradation. Unfortunately, these excipients tend to diffuse away from polymeric implants and cause tolerability issues.

Proteins must maintain highly organized tertiary and quaternary structures to maintain their biological activity. Counter diffusion of water is required, to varying degrees, for the release of drugs from most bioerodible polymeric implants. Hydration of proteins and peptides over prolonged periods of time at physiologic temperature as encountered with sustained or controlled delivery from biodegradable implants can cause denaturation or degradation of the protein.

Botulinum toxin is known to be unstable in neutral and alkaline conditions. Toxoid proteins from inactivated toxin are not only non-therapeutic but can elicit an immune response that renders a patient refractory to toxin therapy.

U.S. Pat. No. 6,440,460 discloses a pharmaceutical composition for the controlled release of therapeutic agents from carboxylic acid ortho ester polymers. The composition contains a pharmaceutically acceptable salt of an acid, which together with the acid R1-COOH liberated from the decomposition of the ortho ester polymer forms a buffer system in a physiologically acceptable pH range. Thus, this patent describes a composition that is effective to maintain a physiologic pH to improve implant tolerability.

U.S. Pat. No. 6,281,015 teaches the delivery of bioactive peptides with transplanted cells through the use of bioerodible microparticulate delivery systems.

U.S. Pat. No. 6,506,399 describes a controlled release system for multiphasic, in vivo release of therapeutic amounts of botulinum toxin in a human patient over a prolonged period of time. The controlled release system can comprise a plurality of botulinum toxin incorporating polymeric microspheres.

Thus, there remains a need for drug delivery systems, such as implants, that are capable of maintaining a neurotoxin in a stabilized form as the implant degrades.

SUMMARY OF THE INVENTION

New compositions and methods for treating patients have been discovered. The present compositions include one or more neurotoxins incorporated into a biodegradable implant. The neurotoxins are maintained in a stabilized form so that a biological activity of the neurotoxins may be maintained for extended periods of time to achieve one or more therapeutic effects. Benefits associated with implants containing a neurotoxin with sustained biological activity would manifest as improved patient compliance, increased quality of life, improved therapeutic outcome and a reduced incidence of side effects and complications.

In one broad embodiment, a biodegradable neurotoxin implant comprises a neurotoxin component, a biodegradable polymer component, and an acidity regulating component. The neurotoxin component is associated with the biodegradable polymer component. For example, the neurotoxin component may be mixed with, blended with, homogenized with, or dispersed in the biodegradable polymer component. The biodegradable polymer component is effective in controlling release of the neurotoxin from the implant when the implant is located in a patient's body. The acidity regulating component is effective in establishing in vivo a pH in the vicinity of the neurotoxin component associated with the implant of less than about 7. For example, the acidity regulating component may be provided in an amount effective in maintaining a pH of the implant to a value less than about 7 when the implant is located in a patient's body.

The neurotoxin component may comprise one or more |neurotoxins|. In certain embodiments, the neurotoxin component comprises a botulinum toxin, such as a botulinum toxin selected from a group consisting of botulinum toxin types A, B, $C_1$, D, E, F, and G. The neurotoxin component may also comprise therapeutically active derivatives of a neurotoxin.

The biodegradable polymer component may include one or more biodegradable polymers. Some examples of suitable biodegradable polymers include polyesters, poly(ortho esters), and polyanhydrides, and mixtures thereof.

The acidity regulating component may include at least one of biodegradable monomers and oligomers. In certain embodiments, the monomers are substantially identical to the monomeric units of the oligomers. In further embodiments, the monomers and the monomeric units of the oligomers are substantially identical to the monomeric units of the biodegradable polymer of the biodegradable polymer component. In other embodiments, the monomers and monomeric units are different from one another.

In one embodiment, a biodegradable neurotoxin implant comprises a neurotoxin component comprising a botulinum toxin type A; a biodegradable polymer component including at least one biodegradable polymer effective in regulating the release of the botulinum toxin type A from the implant; and an acidity regulating component including (i) monomers from which a biodegradable polymer is derived, and (ii) oligomers including monomeric units substantially identical to the monomers.

Each and every feature described herein, and each and every combination of two or more of such features, is included within the scope of the present invention provided that the features included in such a combination are not mutually inconsistent. In addition, any feature or combination of features may be specifically excluded from any embodiment of the present invention.

These and other aspects and advantages of the present invention are apparent in the following detailed description, examples and claims.

DETAILED DESCRIPTION

The following definitions apply herein.

"About" means plus or minus ten percent of the value so qualified.

"Biocompatible" means that there is an insignificant or clinically acceptable inflammatory response at the site of implantation from use of the implant.

"Effective amount" as applied to a biologically active compound, such as a therapeutic agent, means that amount of the compound which is generally sufficient to effect a desired change in the subject. For example, where the desired effect is a flaccid muscle paralysis, an effective amount of the compound, such as a neurotoxin, is that amount which causes at least a substantial paralysis of the desired muscles without causing a substantial paralysis of adjacent muscle of which paralysis is not desired, and without resulting in a significant systemic toxicity reaction.

"Effective amount" as applied to a non-active ingredient constituent of an implant (such as a polymer used for forming a matrix or a coating composition) refers to that amount of the non-active ingredient constituent which is sufficient to positively influence the release of a biologically active agent or therapeutic agent at a desired rate for a desired period of time. For example, where the desired effect is muscle paralysis by using a single implant, the "effective amount" is the amount that can facilitate extending the release over a period of between about 60 days and 6 years. This "effective amount" can be determined based on the teaching in this specification and the general knowledge in the art.

"Implant" means a controlled release (e.g., pulsatile or continuous) composition or drug delivery system. The implant can be, injected, inserted or implanted into a human body.

"Local administration" means direct administration of a therapeutic agent, such as a neurotoxin to a tissue by a non-systemic route. Local administration therefore includes, subcutaneous, intramuscular, intraspinal (i.e. intrathecal and epidural), intracranial, and intraglandular administration. Local administration excludes a systemic route of administration such as oral or intravenous administration.

"Associated with" means mixed with, combined with, blended with, homogenized with, dispersed within, coupled with, or dissolved in.

"Establishing" a pH is defined to mean causing the occurrence of a pH of less than about 7 and/or maintaining a pH of less than about 7 for a period of time, such as (a) between 1 day and 1 year, or (b) maintaining a pH sufficient to prevent formation of an amount of neurotoxin toxoid (e.g., a denatured neurotoxin) capable of causing an immune response in the recipient of the implant.

"Neurotoxin" means an agent which can interrupt nerve impulse transmission across a neuromuscular or neuroglandular junction, block or reduce neuronal exocytosis of a neurotransmitter or alter the action potential at a sodium channel voltage gate of a neuron. Examples of neurotoxins include botulinum toxins, tetanus toxins, saxitoxins, and tetrodotoxin. Neurotoxins in accordance with the disclosure herein are preferably non-cytotoxic, e.g., administration of the neurotoxins does not directly kill or destroy cells that the neurotoxins affect. Neurotoxins specifically exclude toxoids, such as a botulinum toxoid, which may be used as an antigen in order to confer immunity to the neurotoxin through development of antibodies (immune response) due to the immunogenicity of the toxoid.

"Treatment" means any treatment of a disease in a mammal, and includes: (i) preventing the disease from occurring or; (ii) inhibiting the disease, i.e., arresting its development; (iii) relieving the disease, i.e., reducing the incidence of symptoms of or causing regression of the disease.

The present invention involves biodegradable neurotoxin-containing implants that provide therapy to a human or animal patient. In accordance with the disclosure herein, implants are disclosed that are effective in maintaining the stability of the neurotoxin in-vivo as the implant degrades. Thus, the implants provide prolonged periods of therapeutic activity to a human or animal patient that is administered such implants.

In general, the present implants comprise a neurotoxin component, a biodegradable polymer component, and an acidity regulating component. The biodegradable polymer component typically is effective in controlling the release of the neurotoxin from the implant when the implant is located in a patient's body. The acidity regulating component is effective in establishing in vivo a pH in the vicinity of the neurotoxin component associated with the implant of less than about 7. The pH may be the pH of the interior of the implant, or a region around a degrading implant, such as a region encompassing a distance of less than about 10 mm around the implant. In certain embodiments, the acidity regulating component is provided in an amount effective in maintaining a pH of the implant to a value less than about 7, such as less than 7.4, when the implant is located in a patient's body.

The implant can be provided in a variety of forms. In one embodiment, the implant includes a matrix of the neurotoxin component, the biodegradable polymer component, and the acidity regulating component. In another embodiment, the implant may include discrete regions, such as an outer portion and a core portion, with different amounts of one or more of the components of the implant. In yet another embodiment, the implant may include a plurality of pores extending through an otherwise solid material, the pores being effective to facilitate degradation of the implant when the implant is located in a patient's body. Either the neurotoxin component is substantially uniformly distributed in the biodegradable polymer component, the acidity regulating component is substantially uniformly distributed in the biodegradable polymer component, or both the neurotoxin component and the acidity regulating component are substantially uniformly distributed in the biodegradable polymer component.

As described herein, the neurotoxin component may include or comprise a single or one type of neurotoxin, or the neurotoxin component may include a combination of two or more types of neurotoxins. The neurotoxin or neurotoxins of the neurotoxin component may be naturally occurring or synthetic (e.g., they may be produced using recombinant technologies). The neurotoxin component may include therapeutically active derivatives of a neurotoxin. Derivatives include therapeutically active neurotoxin fragments. Neurotoxin derivatives include neurotoxin-like agents that are either structurally or functionally similar to a neurotoxin. Neurotoxin derivatives may be identified using routine methods known by persons of ordinary skill in the art, such as methods that evaluate the potency or lethality of a botulinum toxin, such as a botulinum toxin type A.

In certain embodiments, the neurotoxin component includes a Clostridial neurotoxin, such as a neurotoxin synthesized by one or more of the following bacterium: *Clostridium botulinum, Clostridium butyricum*, and *Clostridium beratti*. In one embodiment, one neurotoxin of the neurotoxin component is a botulinum toxin. More specifically, the neurotoxin component may include one or more botulinum toxins selected from the group consisting of botulinum toxin types A, B, $C_1$, D, E, F, and G. In one specific embodiment, the implant includes a botulinum toxin type A. The botulinum toxins may be naturally occurring or synthetically manufactured, such as recombinant botulinum toxins. In addition, the botulinum toxins may be provided in the implant as a complex, or as isolated toxin preparations. Thus, the neurotoxin component of the implant may consist essentially of a botulinum toxin type A, or a biologically active derivative thereof, or the neurotoxin component may consist essentially of a botulinum toxin type A, and one or more of a botulinum toxin type B, $C_1$, D, E, F, or G.

The amount of neurotoxin that may be provided in the implant is sufficient to achieve a desired therapeutic effect in a patient, e.g., an effective amount. The amount of neurotoxin may be adjusted depending on the condition being treated, the type of neurotoxin being utilized, the duration of treatment, and the number of different neurotoxins present in the implant, among other things. For example, in some embodiments, the implant may comprise an amount of a botulinum toxin between about 1 unit and about 500,000 units. In a more specific embodiment, the implant comprises an amount of botulinum toxin type A between about 10 units and about 2000 units. The quantity of a botulinum toxin required for therapeutic efficacy can be varied according to the known clinical potency of the different botulinum toxin serotypes. For example, several orders of magnitude more units of a botulinum toxin type B are typically required to achieve a physiological effect comparable to that achieved from use of a botulinum toxin type A.

The biodegradable polymer component of the implant may include or comprise a single or one biodegradable polymer, or the biodegradable polymer component may include a combination of two or more different biodegradable polymers. The biodegradable polymer component includes one or more polymers that degrade over time under physiological conditions of different environments in a patient's body.

In certain embodiments, the polymers preferentially degrade at a substantially neutral pH, such as a pH of about 7.2 to about 7.4. In other embodiments, the polymers may have an enhanced or reduced rate of degradation under relatively more acidic conditions. The polymers are preferably biocompatible and do not generate an adverse effect in the patient in which the implant is placed.

In some embodiments, the biodegradable polymer component includes at least one polymer selected from a group of polymers consisting of polyesters, poly (ortho esters), and polyanhydrides. For example, the biodegradable polymer component may comprise a mixture of a polyester and a polyanhydride. More specifically, some implants may include a biodegradable polymer component that comprises at least one polymer selected from the group consisting of poly-lactic acid (PLA), poly (lactic-co-glycolic acid) (PLGA), poly-L-lactic acid (PLLA), polycaprolactone, and poly (ortho acetate). In one embodiment, the biodegradable polymer component of the implant comprises a plurality of different biodegradable polymers.

Other biodegradable polymers suitable for the implant may include polymers of collagens, poly(glycolic acid)s, polycarbonates, polyesteramides, poly(amino acids), polycyanoacrylates, poly(p-dioxanone), poly(alkylene oxalates), biodegradable polyurethanes, blends and copolymers thereof.

Biodegradable PLGA polymers have been used to form resorbable sutures and bone plates and in several commercial microparticle formulations. PLGA may degrade to produce lactic and glycolic acid and is commercially available in a variety of molecular weight and polymer end groups (e.g. lauryl alcohol or free acid). Polyanhydrides are another group of polymers that have been approved for use in humans, and have been used to deliver proteins and antigens. Unlike PLGA, polyanhydrides degrade by surface erosion, releasing neurotoxin entrapped at the carrier surface.

In some embodiments, the biodegradable polymer component of the implant includes a polymer that includes at least one ester bond. Biodegradation of such a polymer occurs by hydrolysis of the at least one ester bond.

The acidity regulating component of the implants disclosed herein are effective in maintaining a substantially acidic environment in proximity to or in the vicinity of the implant. For example, the acidity regulating component may maintain a pH of a microenvironment of the implant, such as one or more interior portions of the implant, at a value less than about 7, such as less than 7.4. In some embodiments, the acidity regulating component is effective in maintaining the pH of the implant in a range of about 3 to about 7. In additional embodiments, the acidity regulating component is effective in maintaining the pH of the implant in a range of about 4 to about 6. Maintaining the pH of the implant to a value less than about 7 is effective in stabilizing the neurotoxin as the implant degrades in the patient. Thus, the therapeutic activity of the neurotoxin, such as the botulinum toxin, is maintained for prolonged periods of time, such as for the life of the implant. The effects obtained with the acidity regulating component may be most prominent in the interior portion of the implant. However, the effects may also be seen in regions around the exterior of the implant, such as within a distance of about 10 mm of a surface of the implant.

In certain embodiments, the stability of the neurotoxin is maintained for at least eighty percent of the life of the implant, and more preferably, at least ninety percent of the life of the implant. In at least one embodiment, the acidity regulating component is effective in establishing the pH of the implant, such as a microenvironment of the implant, below about 7 during the life of the implant.

The acidity regulating component may comprise, consist essentially of, or consist of, either biodegradable monomers, or oligomers, or both. Suitable monomers includes dimmers, such as cyclic dimmers which can rapidly generate monomers in-situ, such as cyclic lactide or cyclic glycolide dimmers. More specifically, the monomers of the acidity regulating component may be monomers from which a biodegradable polymer is derived. For example, the monomers may be substantially similar to monomeric units of the biodegradable polymer of the biodegradable polymer component. Similarly, the oligomers of the acidity regulating component may include monomeric units substantially identical to monomers from which a biodegradable polymer is derived.

In certain embodiments, the oligomers of the acidity regulating component include monomeric units substantially identical to the monomers of the acidity regulating component.

In certain embodiments, the biodegradable polymer of the biodegradable polymer component and the oligomers of the acidity regulating component include monomeric units substantially identical to the monomers of the acidity regulating component.

In other embodiments, the monomeric units of either the biodegradable polymer or the oligomers, or both may be different than the monomers of the acidity regulating component. One feature that the monomers, oligomers, and polymers share is that they are all biodegradable. The monomers and oligomers typically degrade at a relatively faster rate than the polymers or generate acid functionalities at a faster rate, and thus, are effective in maintaining an acidic environment or microenvironment of the implant. The monomers and oligomers remain as discrete elements within the implant.

In certain embodiments, the acidity regulating component includes only monomers from which a biodegradable polymer can be derived. In other embodiments, the acidity regulating component includes only oligomers including monomeric units that are substantially identical to the monomeric units of a biodegradable polymer. In additional embodiments, the acidity regulating component includes a combination of monomers and oligomers.

Thus, in one embodiment, an implant comprises an acidity regulating component that includes at least one of a monomer from which a biodegradable polymer is derived, and an oligomer including monomeric units substantially identical to the monomeric units included in the biodegradable polymer. The biodegradable polymer may be the same or different than the biodegradable polymer of the biodegradable polymer component.

For example, in one embodiment of an implant, the implant includes a biodegradable polymer component that includes a first biodegradable polymer, and the acidity regulating component of the implant includes at least one of monomers from which the first biodegradable polymer is derived, and oligomers including monomeric units substantially identical to monomeric units included in the first biodegradable polymer. In this embodiment, the first biodegradable polymer and the oligomers include monomeric units substantially identical to the monomers of the acidity regulating component.

In another embodiment, the implant includes a biodegradable polymer component that includes a first biodegradable polymer, and an acidity regulating component that includes at least one of monomers from which a second biodegradable polymer is derived, and oligomers including monomeric units substantially identical to the monomeric units included in the second biodegradable polymer. In this embodiment, the monomers and the monomeric units of the oligomers of the acidity regulating component are substantially different than the monomeric units of the first biopolymer.

In yet another embodiment, the biodegradable polymer component of the implant includes a first biodegradable polymer, and the acidity regulating component includes at least one of monomers from which a second biodegradable polymer is derived, and oligomers including monomeric units substantially identical to monomeric units included in a third biodegradable polymer. In this embodiment, the monomers of the acidity regulating component, the monomeric units of the oligomers of the acidity regulating component, and the monomeric units of the biodegradable polymer of the biodegradable polymer component are substantially different from each other. Such an implant may be understood to include an acidity regulating component including at least one of a first monomer, and an oligomer derived from a second mononer different from the first monomer. A biodegradable polymer of the biodegradable polymer component of the implant may be derived from a third monomer that is different from both the first and second monomers.

In another embodiment, the acidity regulating component comprises a combination of monomers and oligomers, in which the oligomers include monomeric units substantially identical to the monomers (e.g., the oligomers of the acidity regulating component are derived or formed from the monomers of the acidity regulating component). The biodegradable polymer of such implants may be selected from the group consisting of polyesters, poly (ortho esters), polyanhydrides, and mixtures thereof. In certain embodiments, the biodegradable polymer of the implant is selected from the group consisting of poly-lactic acid (PLA), poly(lactic-co-glycolic acid) (PLGA), poly-L-lactic acid (PLLA), polycaprolactone, poly(ortho acetate), and mixtures thereof.

The implant disclosed herein may also include a pharmaceutically acceptable excipient as understood by persons of ordinary skill in the art. Some examples of suitable excipients include starch, cellulose, talc, glucose, lactose, sucrose, gelatin, malt, rice, flour, chalk, silica gel, magnesium stearate, sodium stearate, glycerol monostearate, sodium chloride, albumin and dried skim milk.

The implant disclosed herein may also include an acidity regulating component that not only includes monomers from which a biodegradable polymer is derived, but may also include salts of such monomers.

As described herein, the neurotoxin component of the implant may include a botulinum toxin. In one embodiment, the neurotoxin component comprises, consists essentially of, or consists of, a botulinum toxin type A neurotoxin. Botulinum toxin type A is publicly available under the tradename, BOTOX (Allergan, Inc., U.S.) or under the tradename DYSPORT (Ipsen Pharmaceuticals, UK). In another embodiment, the neurotoxin component comprises, consists essentially of, or consists of, a botulinum toxin type B neurotoxin. Botulinum toxin type B is publicly available under the tradename MYOBLOC (Elan Pharmaceuticals). The biodegradable polymer component may include one or more biodegradable polymers. Biodegradable polymers useful in the biodegradable polymer component are publicly available and can be made utilizing conventional chemical processes that are routine to persons of ordinary skill in the art. Similarly, the monomers and oligomers of the acidity regulating component are publicly available and may also be synthesized using routine conventional chemical processes as understood by persons of ordinary skill in the art.

In one embodiment, the various components of the implant, such as the neurotoxin component, the biodegradable polymer component, and the acidity regulating component, are blended together to form the implant. The components may be blended in a liquid to form a liquid composition which is then processed to form an implant suitable for delivery to a patient. One form of processing the blended materials is to extrude the liquid composition to form biodegradable implants. Additionally, the components may be blended as powders and directly extruded into implants. Or, the components may be blended together in a non-liquid form, such as a dry form, to form a non-liquid composition which may then be processed to form an implant suitable for delivery.

In one embodiment, a method of manufacturing a biodegradable neurotoxin implant includes dissolving a biocompatible and biodegradable polymer in a polymer solvent to form a polymer solution. Biologically active, stabilized neurotoxin may then be dispersed in the polymer solution. In addition, biodegradable monomers and oligomers may be added to the polymer solution. The method may further include a step solidifying the biodegradable polymer to form a polymeric matrix containing a dispersion of the neurotoxin, monomers, and oligomers.

By way of example, a biodegradable neurotoxin implant can be made by dissolving a biodegradable polymer in an organic solvent such as methylene chloride or ethyl acetate. Other solvents may include polar organic liquids such as chloroform and acetone. A neurotoxin, such as a botulinum toxin, can then be mixed into the polymer solution.

One method for forming a neurotoxin controlled release composition from a polymer solution is the solvent evaporation method is described in U.S. Pat. Nos. 3,737,337; 3,523,906; 3,691,090; and; 4,389,330. Another method may include one or more steps disclosed in U.S. Pat. No. 5,019,400.

Another method of forming a neurotoxin implant, from a polymer solution, includes film casting, such as in a mold, to form a film or a shape. For instance, after putting the polymer solution containing a dispersion of stabilized neurotoxin into a mold, the polymer solvent is then removed by means known in the art, or the temperature of the polymer solution is reduced, until a film or shape, with a consistent dry weight, is obtained.

In one embodiment, the implant may be understood to include a matrix that comprises the neurotoxin component, the biodegradable polymer component, and the acidity regulating component. Fluids, such as aqueous liquids, can permeate the matrix to degrade biodegradable materials of the implant. As discussed herein, the acidity regulating component typically includes one or more elements that degrade relatively faster than the biodegradable polymer component, and thus, a local pH of the implant can be effectively maintained.

In another embodiment, the implant may include an outer coating of a biodegradable polymer. In such an embodiment, the neurotoxin component and the acidity regulating component may be located in a shell of the biodegradable polymer. In other words, the neurotoxin implant may be understood to include an outer portion and a core portion located in the outer portion. The core portion includes a neurotoxin component, a biodegradable polymer component, and at least one of a monomer from which a biodegradable polymer is derived, and an oligomer including monomeric units substantially identical to the monomer. The outer portion includes a biodegradable polymer component, and may or may not include a neurotoxin component, or an acidity regulating component, as described herein. The core portion also includes an implant microenvironment, such as the interior of the implant. The at least one monomer and the oligomer are effective in controlling a pH of the microenvironment. As discussed herein, the implant may also include combinations of different monomers and oligomers.

In certain embodiments of the implant disclosed herein, the monomers and oligomers of the acidity regulating component are provided in a range of about 0.1% (w/w) to about 30% (w/w). In further embodiments, the monomers and oligomers are provided in a range of about 1% (w/w) to about 20% (w/w). And in still further embodiments, the monomers and oligomers are provided in a range of about 5% (w/w) to about 10% (w/w). In addition, the monomers and oligomers may be provided in different ratios. For example, in certain embodiments, the acidity regulating component may comprise about 95% monomers and about 5% oligomers. In other embodiments, the oligomers may constitute about 95% of the acidity regulating component and the monomers may constitute about 5% of the acidity regulating component. In another embodiment, the monomers and oligomers are provided in a 1:1 ratio. In one embodiment, the acidity regulating component is made up of about 5-45% monomers and about 95-55% oligomers. In another embodiment, the acidity regulating component is made up of about 55-95% monomers and about 5-45% oligomers. Embodiments within the scope of our invention include the acid regulating component being comprised of dimmers or of 100% monomers instead of any oligomers, as well as the where acid regulating component being comprised of 100% oligomers.

In accordance with the disclosure herein, oligomers and monomers of biodegradable polymers such as polyesters, polyanhydrides, or poly (ortho esters) may be provided in an implant to reduce and maintain pH in the implant, such as in a microenvironment of the implant. By establishing a local acidic pH, neurotoxins that are provided in the implant may be stabilized to provide a therapeutic effect for extended periods of time. The neurotoxin component may include wild-type or recombinant neurotoxins, as well as therapeutically active derivatives of such neurotoxins.

While not wishing to be bound by any particular theory or mechanism of action, it is believed that although monomers and oligomers located at the surface of a polymeric implant may diffuse away from the implant when the implant is placed in a body of a patient, monomers and oligomers located in the core of the implant will hydrolyze and maintain a relatively low pH in the implant as it degrades. As indicated herein, an acidic environment may be helpful in maintaining in-vivo stability of proteins and/or peptides, such as neurotoxins, located in the implant.

The implant disclosed herein provides for a controlled and extended release of a neurotoxin, such as a botulinum toxin type A, and complexes thereof, from a biodegradable polymer, such as polyesters, polyanhydrides, and poly (ortho esters). The implant releases a therapeutically effective amount of the neurotoxin over a period ranging from about one month to about two years, without substantial degradation of the neurotoxin. The release of the neurotoxin may be continuous or phasic, such as pulsatile, as disclosed in U.S. Pat. No. 6,506,399.

The implants disclosed herein may be used by placing the implants in or administering the implants to a patient. For example, the implants may be administered to a patient by injecting the patient with a needle and delivering a suspension containing the implant into the patient. Alternatively, implants may be placed at one or more locations using a surgical procedure to access a desired target site. The implant can be implanted subcutaneously, intramuscularly, intracranially, intraglandularly, etc, at a site so that systemic entry of the toxin is not encouraged. The implant can provide a therapeutically effective amount or amounts of biologically active neurotoxin for prolonged periods of time.

Thus, an implant can be administered to a human, or other animal, by any non-systemic means of administration, such as by implantation (e.g. subcutaneously, intramuscularly, intracranially, intravaginally and intradermally), to provide the desired dosage of neurotoxin based on the known parameters for treatment with neurotoxin of various medical conditions, as previously set forth. Methods for determining the appropriate route of administration and dosage are generally determined on a case by case basis by the attending physician. Such determinations are routine to one of ordinary skill in the art (see for example, Harrison's Principles of Internal Medicine (1998), edited by Anthony Fauci et al., 14.sup.th edition, published by McGraw Hill).

The specific dosage by an implant appropriate for administration is readily determined by one of ordinary skill in the art according to the factors discussed above. The dosage can also depend upon the size of the tissue mass to be treated or denervated, and the commercial preparation of the toxin. Additionally, the estimates for appropriate dosages in humans can be extrapolated from determinations of the amounts of botulinum required for effective denervation of other tissues. Thus, the amount of botulinum A to be injected is proportional to the mass and level of activity of the tissue to be treated. Generally, between about 0.01 units per kilogram to about 35 units per kg of patient weight of a botulinum toxin, such as botulinum toxin type A, can be released by the present implant per unit time period (i.e. over a period of or once every 2-4 months) to effectively accomplish a desired muscle paralysis. Less than about 0.01 U/kg of a botulinum toxin may not have a significant therapeutic effect upon a muscle, while more than about 35 U/kg of a botulinum toxin may approach a toxic dose of a neurotoxin, such as a botulinum toxin type A.

Careful preparation and placement of the implant prevents significant amounts of a botulinum toxin from appearing systemically. A more preferred dose range is from about 0.01 U/kg to about 25 U/kg of a botulinum toxin, such as that formulated as BOTOX®. The actual amount of U/kg of a botulinum toxin to be administered depends upon factors such as the extent (mass) and level of activity of the tissue to be treated and the administration route chosen.

The implants may be effective in treating any condition which may be susceptible to neurotoxin therapy. For example, the implants of the present invention provide an extended release of small amounts of a stabilized neurotoxin, such as a stabilized botulinum toxin from the implant so as to inhibit exocytosis in-vivo and thereby achieve a desired therapeutic effect, such as reduction of muscle spasm or muscle tone, preventing a muscle from contracting or to reduce an excessive secretion (i.e. a sweat secretion) from a cholinergically influenced secretory cell or gland. The implant may be effective in treating acute or chronic disorders, such as movement disorders. In addition, the implants may be effective in providing cosmetic benefits, such as a reduction of wrinkles, to patients for extended periods of time.

The present invention also includes within its scope the use of a neurotoxin, such as a botulinum toxin, in the preparation of a medicament, such as a biodegradable neurotoxin implant, for the treatment of a movement disorder, and/or a disorder, including cosmetic defects, influenced by cholinergic innervation, by local administration via the implant of the neurotoxin.

EXAMPLES

The following examples illustrate embodiments and aspects of the present invention and are not intended to limit the scope of the present invention.

Example 1

Method for Making a Stabilized Botulinum Toxin Compressed Tablet Implant

A biodegradable implant comprising a stabilized botulinum toxin is prepared by combining a botulinum toxin, a biodegradable polymeric material, and biodegradable monomers and oligomers. The botulinum toxin is obtained from Allergan, Inc. under the tradename, BOTOX. Poly(D,L-lactide-co-glycolide) (PLGA) is obtained from Boehringer Ingelheim, Inc. Monomers and oligomers of PLGA are prepared by hydrolyzing the PLGA.

Lyophilized botulinum toxin (BOTOX, Allergan, Inc.), micronized hydrophobic end 48:52 to 52:48 PLGA, and monomers and oligomers obtained from PLGA are weighed and placed in a mixing vessel. The vessel is sealed, placed on a mixer and mixed at a prescribed intensity, e.g., 96 rpm, and time, e.g., 15 minutes. The resulting powder blend is loaded one unit dose at a time into a single-cavity tablet press. The press is activated at a pre-set pressure, e.g., 25 psi, and duration, e.g., 6 seconds, and the tablet is formed and ejected from the press at room temperature. The implant contains about 100 units of BOTOX, and a ratio of 60:40 of the monomers to oligomers. The monomers and oligomers constitute 25% w/w of the implant.

Example 2

Method for Making a Stabilized Botulinum Toxin Extruded Implant

BOTOX, unmicronized PLGA, and monomers and oligomers obtained from PLGA are weighed and placed in a mixing vessel. The vessel is sealed, placed on a mixer and mixed at a prescribed intensity, e.g., 96 rpm, and time, e.g., 10-15 minutes. The unmicronized PLGA composition comprises a 30/10 w/w mixture of hydrophilic end PLGA (Boehringer Ingelheim, Wallingford, Conn.) and hydrophobic end PLGA (Boehringer Ingelheim, Wallingford, Conn.). The resulting powder blend is fed into an extruder, such as a DACA Microcompounder-Extruder (DACA, Goleta, Calif.), and subjected to a pre-set temperature. To reduce denaturation of the BOTOX, the temperature is typically less than 37° C. The screw speed of the extruder is about 12 rpm. The filament is extruded into a guide mechanism and cut into lengths corresponding to the designated implant weight. The extruded implants contain about 500 units of BOTOX, and about 20% w/w of monomers and oligomers of PLGA. The monomers to oligomer ratio is 70:30.

Example 3

Method for Making a Stabilized Botulinum Toxin Extruded Implant with Polylactide Polymers An extruded implant is prepared as described in Example 2, except the PLGA is replaced with a polylactide polymer. The implant contains 100 units of BOTOX, and about 15% w/w of the monomers and oligomers of PLGA. The ratio of monomers to oligomers is 10:90.

Example 4

Method for Making a Stabilized Botulinum Toxin Extruded Implant with Poly-L-lactide Polymers An implant is made as described in Example 2 except the PLGA is replaced with a poly-L-lactide (PLLA) polymer. Implants are sized to have between 100 and 2000 units of BOTOX, and about 0.1% w/w of the monomers and oliogomers of PLGA. The ratio of monomers to oligomers is 80:20.

Example 5

Method for Inserting an Implant into the Vitreous

An implant is surgically implanted into the posterior segment of a human eye through an incision in the pars plana inferotemporally. A sterile trocar, preloaded with a 5 unit or 10 unit botulinum toxin ocular implant can be inserted 5 mm through the sclerotomy, and then retracted with the push wire in place, leaving the implant in the posterior segment. Sclerae and conjunctivae can then be closed using a 7-0 Vicryl suture. After closure, the suture knot can be buried and subconjunctival and topical antibiotics used prophylactically. Such an intraviteal implant can be used to treat a variety of ocular disorders such as macular edema, uveitis, macular degeneration, retinal detachment, ocular tumors, ocular fungal or viral infections, multifocal choroiditis, diabetic retinopathy, proliferative vitreoretinopathy, sympathetic opthalmia, Vogt Koyanagi-Harada syndrome, histoplasmosis, uveal diffusion, and ocular vascular occlusion. The implant includes a combination of biodegradable monomer and oligomers that are effective in establishing an acidic environment around the implant. The botulinum toxin is effective for at least four months, until the implant is substantially completely degraded.

Example 6

Treatment of Pain Subsequent to Limb Injury by with an Implant

A patient, age 35, experiencing pain subsequent to injury to his hand, arm, foot or leg is treated by placing an extruded implant as described in Examples 2-4 in a muscular region near the site of injury. The implant includes between 20 units and 500 units of botulinum toxin type A. The particular size of the implant, dose and target site depend upon a variety of factors within the skill of the treating physician. Within 1-7 days after administration the patient's pain is substantially alleviated. The duration of pain reduction is from about 6 months to 1 year.

Example 7

Treatment of Osteoid Osteoma with a Botulinum Toxin Implant

A 24 year-old female presents with a four month history of pain in the right buttock radiating to the lateral aspect of her thigh and leg. The pain is throbbing in nature and awakens her at night. It is aggravated by exercise and partially alleviated by aspirin. Examination reveals a full range of hip motion. Routine lab values (hematocrit, WBC, etc.) and CSF content are normal. Pelvic X-rays reveal a small, oval lesion at the base of the right femoral neck. A diagnosis of osteoid osteoma is made. Under radiographic guidance an implant as described above is placed adjacent the tumor. Within 1 to 7 days the pain has been alleviated by about 60%. Radiography and bone aspiration biopsy at 6 months, 12 months, and 24 months, post injection fails to reveal any evidence of the neoplasm.

Example 8

Treatment of Cosmetic Defects with a Botulinum Toxin Implant

Any of the implants of Examples 1-4 are used to treat cosmetic defects. When the cosmetic defects are located on a person's face, the implants are produced to provide a dose of botulinum toxin type A from about 20 unit to about 500 units for a prolonged period of time. The implants are small so that they may be placed subdermally near a muscle region causing the cosmetic defects without being visually noticeable to other people. The implants provide a prolonged release of botulinum toxin in therapeutically effective amounts to treat the cosmetic defect. Thus the implants are effective in treating facial wrinkles, brow furrows, crows feet, strabismus, downturned corners of a mouth, nasolabial folds, lip lines, and the like.

All references, articles, publications and patents and patent applications cited herein are incorporated by reference in their entireties.

While this invention has been described with respect to various specific examples and embodiments, it is to be understood that the invention is not limited thereto and that it can be variously practiced within the scope of the following claims.

What is claimed is:

1. A biodegradable neurotoxin implant, comprising: a neurotoxin component associated with; a biodegradable polymer component; and an acidity regulating component effective in establishing in vivo a pH in the vicinity of the neurotoxin component associated with the implant of less than about 7, wherein the acidity regulating component comprises a monomer and an oligomer derived from the same biodegradable polymer and said monomer and oligomers are provided in a range of about 0.1% (w/w) to about 30%(w/w) of the biodegradable neurotoxin implant.

2. The implant of claim 1, wherein the neurotoxin component comprises a Clostridial neurotoxin.

3. The implant of claim 1, wherein the neurotoxin component comprises a botulinum toxin.

4. The implant of claim 1, wherein the neurotoxin component comprises a botulinum toxin selected from the group consisting of botulinum toxin types A, B, $C_1$, D, E, F, and G, and mixtures thereof.

5. The implant of claim 1, wherein the implant comprises an amount of a botulinum toxin between about 1 unit and about 500,000 units.

6. The implant of claim 1, wherein the implant comprises an amount of a botulinum toxin type A between about 10 units and about 2000 units.

7. The implant of claim 1, wherein the biodegradable polymer component is effective in controlling release of the neurotoxin from the implant when the implant is located in a patient's body.

8. The implant of claim 1, wherein the biodegradable polymer component includes a polymer selected from the group consisting of polyesters, poly(ortho esters), and polyanhydrides, and mixtures thereof.

9. The implant of claim 1, wherein the biodegradable polymer component comprises at least one polymer selected from the group consisting of poly-lactic acid (PLA), poly(lactide-co-glycolide)acid (PLGA), poly-1-lactic acid (PLLA), poly-caprolactone, and poly(ortho acetate), and mixtures thereof.

10. The implant of claim 1, wherein the biodegradable polymer component includes a polymer that includes at least one ester bond, and biodegradation of the polymer occurs by hydrolysis of the at least one ester bond.

11. The implant of claim 1, wherein the acidity regulating component is provided in an amount effective in maintaining a pH of the implant to a value less than about 7 when the implant is located in a patient's body.

12. The implant of claim 1, wherein the acidity regulating component is effective in maintaining the pH of the implant in a range of about 3 to about 7.

13. The implant of claim 1, wherein the acidity regulating component is effective in maintaining the pH of the implant in a range of about 4 to about 6.

14. The implant of claim 1, wherein the acidity regulating component is effective in stabilizing the neurotoxin as the implant biodegrades.

15. The implant of claim 1, wherein the acidity regulating component is effective in maintaining the neurotoxin in a stabilized form during the life of the implant.

16. The implant of claim 1, wherein the biodegradable polymer is selected from the group consisting of polyesters, poly(ortho esters), polyanhydrides, and mixtures thereof.

17. The implant of claim 1, further comprising a pharmaceutically acceptable excipient.

18. The implant of claim 1, wherein the acidity regulating component comprises monomers from which a biodegradable polymer is derived, and the implant further comprises salts of the monomers.

19. The implant of claim 1, wherein the neurotoxin component comprises a botulinum toxin type A.

20. A biodegradable neurotoxin implant, comprising: a neurotoxin component comprising a botulinum toxin type A; a biodegradable polymer component including at least one biodegradable polymer effective in regulating the release of the botulinum toxin type A from the implant; and an acidity regulating component including a monomer and an oligomer derived from the same biodegradable polymer and said monomer and oligomers are provided in a range of about 0.1% (w/w) to about 30%(w/w) of the biodegradable neurotoxin implant.

21. The implant of claim 20, wherein the biodegradable polymer component includes a plurality of different biodegradable polymers.

22. A method of making the implant of claim 20, comprising a step of blending the neurotoxin component, the biodegradable polymer component, and the acidity regulating component together.

23. The implant of claim 1, wherein said monomers and oligomers of said acidity regulating component are together about 25%, 20%, 15%, or 0.1% by weight of said biodegradable polymer component.

24. The implant of claim 1, wherein the ratio of said monomers and oligomers of said acidity regulating component is about 60:40, 70:30, 10:90 or 80:20.

25. The implant of claim 1, wherein said monomers and oligomers of said acidity regulating component are together about 25%, 20%, 15%, or 0.1% by weight of said biodegradable polymer component and the ratio of said monomers and oligomers of said acidity regulating component is about 60:40, 70:30, 10:90 or 80:20.

* * * * *

UNITED STATES PATENT AND TRADEMARK OFFICE
CERTIFICATE OF CORRECTION

PATENT NO. : 7,691,381 B2  Page 1 of 1
APPLICATION NO. : 10/826441
DATED : April 6, 2010
INVENTOR(S) : Patrick M. Hughes et al.

It is certified that error appears in the above-identified patent and that said Letters Patent is hereby corrected as shown below:

On page 2, under "Other Publications", column 2, line 1, delete "nurotixons:" and insert -- neurotoxins: --, therefor.

On page 2, under "Other Publications", column 2, line 20, delete "Pharmnacol." and insert -- Pharmacol. --, therefor.

In column 3, line 23, delete "hemaglutinin" and insert -- hemagglutinin --, therefor.

In column 3, line 24, delete "nonhemaglutinin" and insert -- nonhemagglutinin --, therefor.

In column 5, line 57, delete "supercihii" and insert -- supercilii --, therefor.

In column 6, line 7, delete "sublimus:" and insert -- sublimis: --, therefor.

In column 7, line 33, delete "b" and insert -- be --, therefor.

In column 7, line 34, delete "terapeutic" and insert -- therapeutic --, therefor.

In column 9, line 4-5, delete "biodgradable" and insert -- biodegradable --, therefor.

In column 9, line 18, delete "|neurotoxins|." and insert -- neurotoxins. --, therefor.

In column 14, line 43, delete "mononer" and insert -- monomer --, therefor.

In column 19, line 33-34, delete "oliogomers" and insert -- oligomers --, therefor.

In column 19, line 49, delete "intraviteal" and insert -- intravitreal --, therefor.

In column 19, line 52, delete "opthalmia," and insert -- ophthalmia, --, therefor.

In column 19, line 55, delete "monomer" and insert -- monomers --, therefor.

Signed and Sealed this

Tenth Day of August, 2010

David J. Kappos
*Director of the United States Patent and Trademark Office*